United States Patent
Zagorchev et al.

(10) Patent No.: US 8,660,633 B2
(45) Date of Patent: Feb. 25, 2014

(54) SMALL ANIMAL IMAGING CAPSULE AND BED SYSTEM

(75) Inventors: Lyubomir Zagorchev, Lebanon, NH (US); Andrew Buckler, Wenham, MA (US); Eric Jean, Woburn, MA (US); Antonio T. Latto, Wakefield, MA (US)

(73) Assignee: Koninklijke Philips N.V., Eindhoven (NL)

(*) Notice: Subject to any disclaimer, the term of this patent is extended or adjusted under 35 U.S.C. 154(b) by 839 days.

(21) Appl. No.: 12/600,669

(22) PCT Filed: May 6, 2008

(86) PCT No.: PCT/IB2008/051763
§ 371 (c)(1),
(2), (4) Date: Apr. 20, 2010

(87) PCT Pub. No.: WO2008/142593
PCT Pub. Date: Nov. 27, 2008

(65) Prior Publication Data
US 2010/0198047 A1    Aug. 5, 2010

Related U.S. Application Data

(60) Provisional application No. 60/939,866, filed on May 24, 2007.

(51) Int. Cl.
*A61B 5/00* (2006.01)
(52) U.S. Cl.
USPC ........... 600/407; 600/411; 600/415; 600/427; 600/436; 5/601; 119/417; 119/452; 119/751; 128/910
(58) Field of Classification Search
USPC ......... 600/407, 410, 411, 414, 421, 425, 426, 600/427, 436; 5/600, 601
See application file for complete search history.

(56) References Cited

U.S. PATENT DOCUMENTS 7,146,936 B2    12/2006  Dazai et al.
7,190,991 B2 *   3/2007  Cable et al. .................. 600/407
(Continued)

FOREIGN PATENT DOCUMENTS

FR      2879094 A1    6/2006
WO   2006/020896 A2   2/2006
(Continued)

OTHER PUBLICATIONS

J Dazai, NA Bock, BJ Nieman, LM Davidson, RM Henkleman, XJ Chen. Multiple Mouse Biological Loading and Monitoring System for MRI. Magnetic Resonance in Medicine 52: 709-715 (2004).*

(Continued)

*Primary Examiner* — Unsu Jung
*Assistant Examiner* — Amanda Lauritzen Moher

(57) ABSTRACT

In a small animal imaging system (10) at least one modality (12) and a docking station (36) are provided. The docking station (36) provides a workspace (47) and docking ports (48) for preparation and holding of anesthetized animals that are awaiting imaging. For the duplication of positions, a subject mold (26) is provided that holds the subject in a reproducible position on a subject bed (16). Vital signs monitoring is also provided for subjects awaiting scans. The bed (16) includes fiducials (28) to aid in registration of like modality images and different modality images. A capsule (14) can encapsulate a single bed (16), or for tandem imaging, the capsule can encapsulate multiple-bed configurations, such as two, three, or four beds (16). For better positioning and ease of user access, a positioner (34) positions the capsule (14) from the rear of the modality (12).

24 Claims, 8 Drawing Sheets

(56) References Cited

U.S. PATENT DOCUMENTS

| | | |
|---|---|---|
| 7,269,516 B2 * | 9/2007 | Brunner et al. ................. 702/19 |
| 7,865,226 B2 * | 1/2011 | Chiodo ......................... 600/407 |
| 7,992,523 B1 * | 8/2011 | Pugh ............................. 119/751 |
| 2001/0044588 A1 * | 11/2001 | Mault ........................... 600/549 |
| 2007/0238946 A1 | 10/2007 | Chiodo |
| 2009/0000567 A1 * | 1/2009 | Hadjioannou et al. ........ 119/755 |

FOREIGN PATENT DOCUMENTS

| | | |
|---|---|---|
| WO | 2007089641 A2 | 8/2007 |
| WO | 2007143401 A2 | 12/2007 |

OTHER PUBLICATIONS

Yap, et al, "Combined Clinical PET/CT and microPET(R) Small Animal Imaging", IEEE Nuclear Science Symposium, 2004, pp. 2995-2998.

Yang, et al. "Multimodality Imaging Combinationin Small Animal via Point-Based Registration", Nuclear Instruments & Methods in Physics Research Sec-A, 569(2), pp. 240-244, Dec. 20, 2006 (Abstract).

* cited by examiner

SMALL ANIMAL IMAGING CAPSULE AND BED SYSTEM

CROSS REFERENCE TO RELATED APPLICATIONS

This application claims the benefit of U.S. provisional application Ser. No. 60/939,866 filed May 24, 2007, which is incorporated herein by reference.

The present application relates to diagnostic imaging of small animals. More specifically, it relates to control of imaging variables across many scans to aid in the quantification and reproducibility of imaging studies, and will be described with particular reference thereto. It is to be understood, however, that the present application can also be applied to other diagnostic imaging applications.

Investigation of in vivo models of disease is enhanced if studies are conducted using reproducible imaging of individual or groups of subjects. Objective control over factors that affect the imaging is desired for quantification and validation of results. Various biological functions affect imaging and it is desirable to either control or monitor these functions through potentially long time periods and across heterogeneous imaging steps if the results are to be used in quantitative studies. Existing monitors and controls are tedious and error prone to set up and cannot be moved between imaging procedures.

Small animal imaging modalities, such as PET and CT, provide unique opportunities for imaging of models of disease implanted in genetically altered animals. Small animal PET for example, is a functional imaging modality that provides valuable insights into biochemical, physiological, and pharmacological processes in vivo. Current applications include perfusion, metabolism and substrate utilization in vital organs such as heart and brain, gene expression, tumor biology and angiogenesis, hypoxia and apoptosis, among many others. Small animal CT on the other hand, is a structural imaging modality that provides high bone to soft tissue contrast. It is used for screening of anatomical abnormalities, differentiation of tumors from normal tissues in angiogenesis, visualization of neo-vascularization with the aid of contrast agents, and etc.

Researchers working with small animal PET and small animal CT perform imaging of small animals such as mice and rats. The investigation and validation of in vivo models of disease require serial imaging of the same or groups of animals over time. A common goal of such studies is to compare and track the progression of disease by using the complementary information provided by the two imaging modalities. Consequently, quantification and accurate assessment of experimental results cannot be achieved without image registration that aligns the acquired volumes in the same coordinate space. Given the practical and logistical limitations of current small animal nuclear, CT, and MRI devices, it is customary to image a single animal at a time whereas it would be beneficial to be able to image multiple animals at the same time for the inclusion of one or more control animals and/or to process multiple animals in parallel for increased throughput.

The present application provides a new and improved small animal imaging handler which overcomes the above-referenced problems and others.

In accordance with one aspect, a diagnostic imaging system is provided. At least one imaging module acquires diagnostic imaging data of a subject in an imaging region of the module, the module having at least a first docking interface. A user prepares the subject at a docking station in preparation for imaging in the imaging module. The docking station has at least a second docking interface. At least one animal capsule encapsulates the subject and interfaces with the first and second docking interfaces. The capsule can come in different sizes and shapes, to accommodate different types of animals (e.g. rats, mice) additional animals in the same capsule (e.g. two rats, two, three or four mice) or different modalities.

In accordance with another aspect, a method of diagnostic imaging is provided. A conscious animal is placed in an induction chamber to anesthetize the animal. The anesthetized animal is mounted to a subject support. The animal is secured and positioned with a mold. A cover is placed about the support, encapsulating the animal. The support is docked at a docking interface of a docking station in a time period following preparation of the animal and before imaging of the animal. The support is removed from the docking station and docked with a docking interface of an imaging modality. At least one diagnostic imaging sequence of the animal on the support is initiated. The animal is then removed from the support after the imaging sequence is complete. The animal regains consciousness in a post-anesthesia chamber to allow the animal to recover from anesthesia.

One advantage is increased subject throughput.

Another advantage lies in the ability to control variables that affect the reproducibility or quantifiability of the study, such as but not limited to, body core temperature and depth of anesthesia.

Another advantage is the ability to image multiple animals at the same time to enable comparison studies.

Another advantage lies in improved monitoring of physiological parameters that may be used in evaluating the study results.

Another advantage lies in use of monitored parameters to raise alarms or alerts that may affect imaging results or subject health.

Another advantage lies in the ability of imaging researchers to move freely between imaging steps allowing a more effective use of the laboratory area.

Another advantage lies in more accurate registration of diagnostic images.

Another advantage lies in improved statistical confidence in the analysis of collected imaging data.

Another advantage lies in environmental control of animals awaiting imaging.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
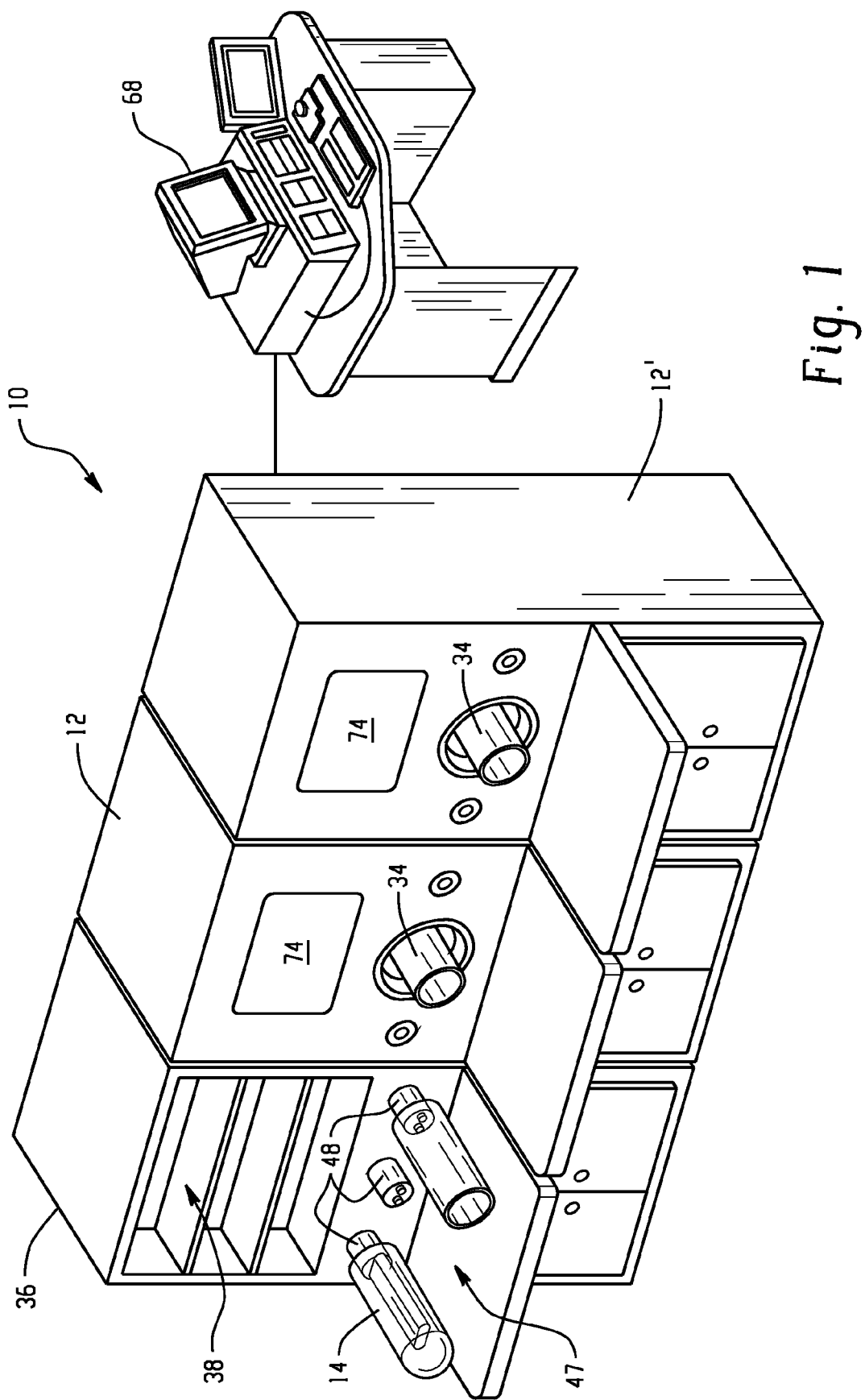
FIG. 1 is a diagrammatic illustration of an animal imaging system, in accordance with the present application.

With reference to FIG. 1, an exemplary small animal imaging system 10 is shown. The present application contemplates a system with modules for positron emission tomography (PET), Computed Tomography (CT), single photon emission computed tomography (SPECT), other diagnostic imaging modules, animal preparation, and a computer workstation for visualization, image registration, fusion, and analysis capabilities. The various modules are combined within a cover that allows flexible configurations with various combinations of side-by-side configurations, determined by space and throughput issues. A common animal positioner is also contemplated, as well as an animal holder that can be docked and undocked against the positioner. In a side-by side configuration, as shown in FIG. 1, accurate image registration is achieved through the docking feature, which provides positional accuracy and repeatability when the animal holder is docked and undocked. Additional image registration can be obtained through the use of fiducial markers.

Figure 2:
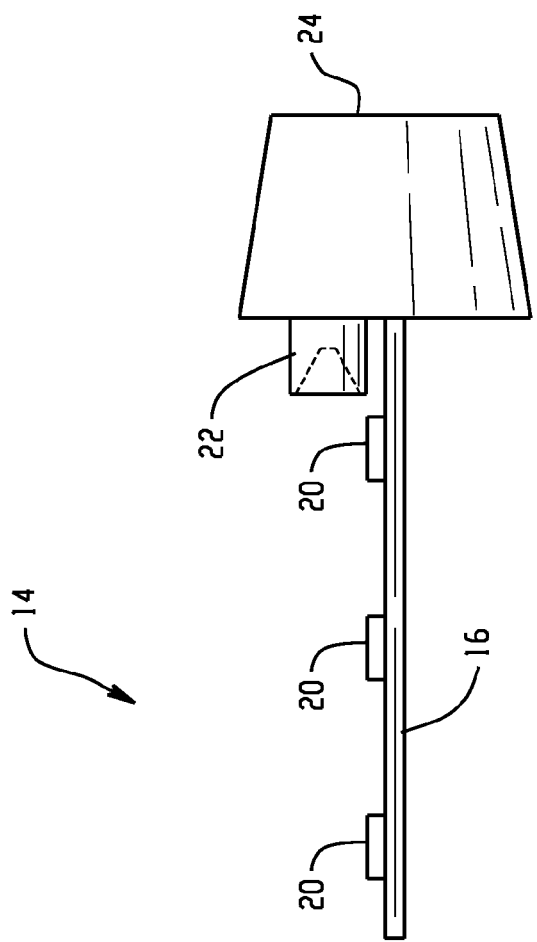
FIG. 2 is a profile view of an animal imaging capsule.
Figure 2:
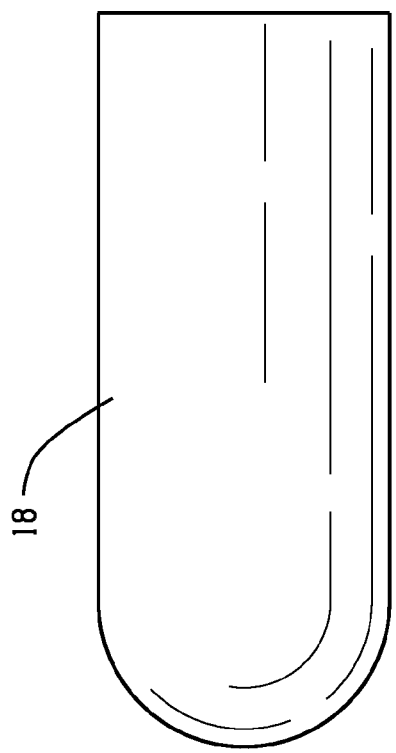

With reference to FIG. 2 continuing reference to FIG. 1, an imaging modality 12 is responsible for imaging data acquisition. As mentioned above, the modality 12 can be any imaging modality, including but not limited to one or more of PET, SPECT, CT, and MRI. Depicted in FIG. 1 is a second modality 12', different than the first modality 12. An animal capsule 14 holds one or more animals during imaging sessions. The capsule 14 typically includes one or more holders, or beds 16, a cylindrical cover 18, physiological parameter sensors 20, provisions for anesthesia 22, such as a nose cone into which the animal's nose fits, and a holder-side docking interface 24. The docking interface 24 is preferably designed in such way that minimal insert/twist force is applied when the holder is inserted into the imaging modality 12. It is preferable that the position of an animal is not disturbed when it is transferred from one modality to another. The docking interface 24 provides monitoring, heating and anesthesia interfaces to the capsule 14. Detection of animal capsule 14 attachment and presence of animals inside the handlers can be done based on monitoring results. For example, if there are no ECG or respiration signals coming from a capsule 14, it is assumed that there is no animal within the capsule. If no animal is detected within a capsule 14, the capsule 14 can be considered disconnected. This check may result in e.g. adjusting user interface's properties so that all displayed/entered information is limited according to the number of detected animals. Also, this information may be used to recognize the current configuration of the modality 12.

This interface 24 preferably supports up to four animals, but more interfaces are certainly contemplated. By configuring all the modalities and docking stations with a uniform docking interface 24, the user can exchange the holder between different modalities and docking stations. Docking interface functionality includes providing monitoring, heating and anesthesia interface to the capsule 14. For safety reasons, the anesthesia valves can be automatically shut off when the capsule 14 is detached and can be reopened when it is attached, e.g. check valves. The capsules are preferably constructed to withstand many cleanings and sterilizations, e.g., alcohol, steam, radiation, and the like.

Figure 3:
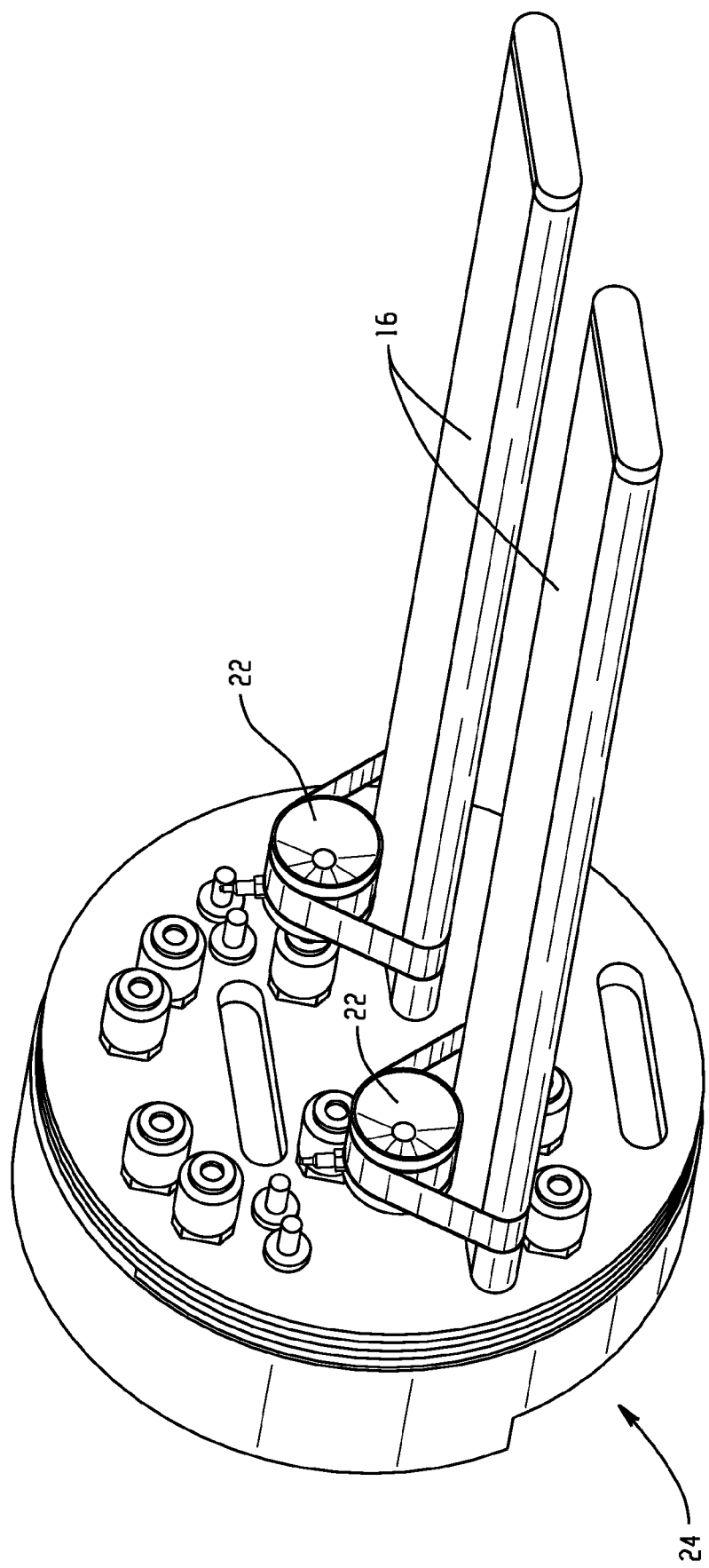
FIG. 3 is a perspective view of a two bed embodiment.
Figure 4:
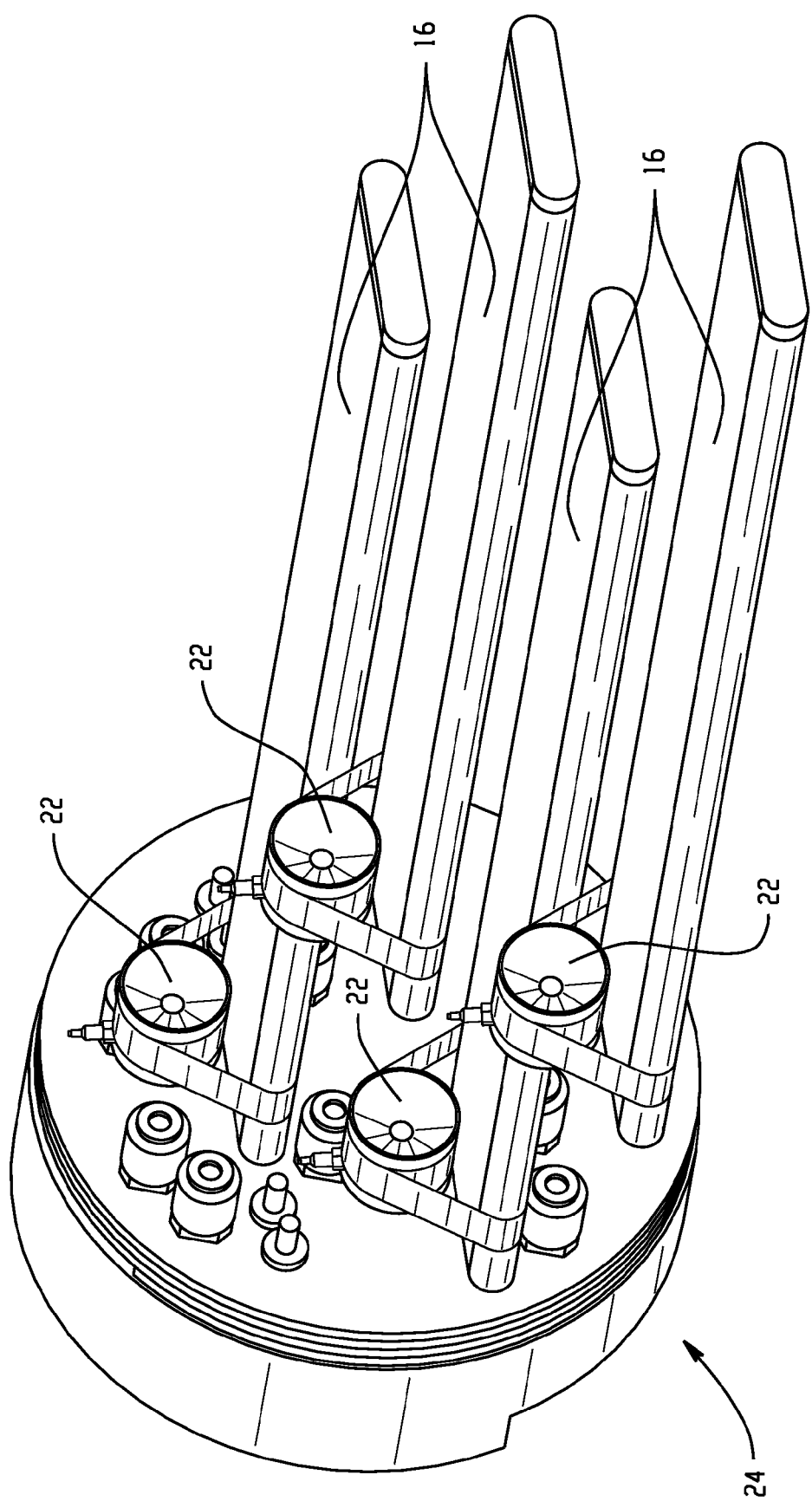
FIG. 4 is a perspective view of a four bed embodiment.

A single animal capsule 14 can support several different bed 16 configurations. One capsule 14 can accommodate up to two (2) rat beds 16, and alternatively, one capsule 14 can accommodate up to four (4) mouse beds 16, that is, one two, three, or four mice could be accommodated in on capsule. A two-bed embodiment is shown in FIG. 3, and a four-bed embodiment is shown in FIG. 4. Apart from at least one bed mount, each of the capsule interfaces 24 also provides one or more sockets connected with the measurement sensors 20, a fluid interface for air and anesthesia, and the like. The beds 16 can be either profiled beds or flat pallets. For increasing heating efficiency, it is preferable that separate and as small as possible cylinders 18 be used around each of the animals instead of one large cylinder 18 covering all the animals, although the latter embodiment is by no means unviable. The cylinders 18 are preferably easily removable. Holes are also provided, through which it is possible to insert or pull out catheters for isotope injection and/or optional measurements and physical interactions.

A flat pallet bed type allows animal technicians to work with non-standard measurements or with non-commonly used animals or animal configurations. The technicians can freely place different animals of different sizes and weights. The nosecone 22 on the pallet bed 16 preferably is interchangeable to accommodate different sizes of animals. The nosecone 22 is preferably radio-translucent and tightly covers the animal's head. Additionally, the nosecone 22 can be removed, e.g. if an injected anesthesia is used. The pallet bed 16 is equipped with holes at each side for mounting motion restraints.

In another embodiment, the bed 16 is a form fitting, profiled bed. The profiled bed 16 preferably comes in a few types, each adjusted to different animal category (rats, mice) and sizes (small, medium, large). The bed curves allows for easy and repeatable animal positioning, both with the same subject in temporally remote scans, or with different subjects. Motion restraints are integrated into the bed to prevent re-arrangement of the subject during or between scans. Restraints integrated with the bed 16 are also contemplated in lieu of traditional taping and un-taping.

Figure 5:
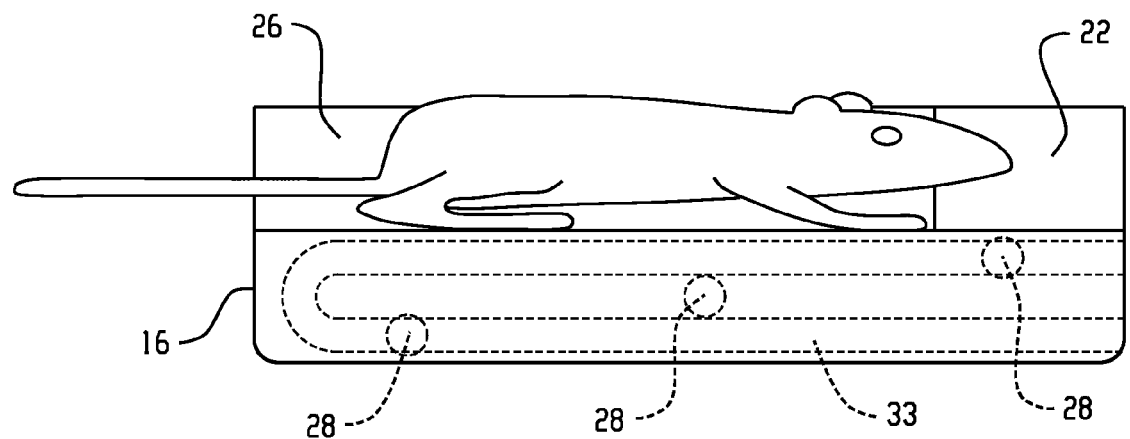
FIG. 5 is a profile view of an animal support bed with a corresponding positioning mold.

With reference to FIG. 5, for purposes of positioning subjects in reproducible positions, and to aid registration of images, a mold 26 is made of a subject. Silicone rubbers are contemporary materials available for making molds and have a very good chemical resistance and a high temperature resistance (205° C. and higher). Small animals such as mice and rats are substantially standard in weight and have very small variation in size and shape. For example, the average body weight of an athymic mouse is 20 grams with a small standard deviation of 2 grams. By placing an animal on the larger end of the scale in a container of silicone rubber a technician can produce an external mold 26 of the animal body. The mold 26 is then cured and attached to the small animal imaging bed 16. A set of molds custom fitted to general shape of the imaged animals (e.g. mice, rats, guinea pigs, etc.) can be prepared similarly and used interchangeably as needed. Imaging different animals placed in the same mold 26 on the imaging bed 16 keeps their shape, orientation, and position relatively similar, significantly simplifying intra-subject rigid or elastic matching of serially acquired volumes of the same animal as well as inter-subject registration.

Figure 6:
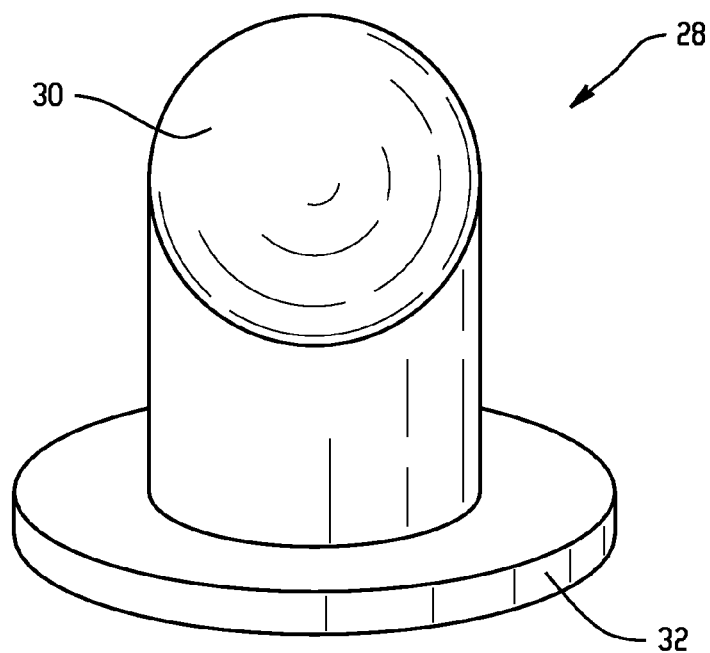
FIG. 6 depicts an exemplary fiducial for the bed of FIG. 5.

To further aid registration of both intra- and inter-subject images, non-radioactive fiducial markers 28 are attached to the bed 16 to provide support for image based rigid or elastic registration techniques. An exemplary fiducial marker 28 is shown in FIG. 6. Solid copper may serve as a fiducial marker in CT, PET, and SPECT. Small spheres or wires of copper 30 are visible in CT while neutron activation of these same markers produces positron-emitting Copper-64 for detection by PET and SPECT. Copper is easily machined into desirable shapes, and prior to activation, is easy and safe to handle. The center of fiducial markers 28 with spherical shapes is easily detected by a Hough transform or another image processing technique such as edge detection followed by a centroid calculation. The process is fully automatic, robust and reliable. After the centers of the fiducial markers 28 are detected, a least squares algorithm for rigid registration can be applied to serially acquired images to correct for a global rigid alignment. Once the partial images are brought into rough alignment, elastic matching can be applied to correct the non-rigid deformations between the volumes that in this case will be constrained by the holder mold 26 custom fitted to the shape of the imaged animal. A base 32 of the fiducial markers 28 can be made in such a way that allows the markers 28 to be attached only if needed. It is also preferred that the fiducials 28 are placed in non-linear and non-planar locations. Optionally, the fiducial 28 includes a hollow copper sphere filled with an MR imageable substance, such as copper sulfate, doped water, hydrogen containing gel or plastic, or the like.

The sensors 20, such as ECG and respiration probes are preferably integrated with the bed 16. Alternately, sensors can be applied to the subject manually. $SpO_2$ and heating elements may also be parts of the bed 16. Position marks on the bed (i.e. ruler-like markings) assist in reproducing positions when mounting subjects to the bed 16. Given that exact repositioning is desirable in brain imaging, a stereotactic frame may be included. To allow access to the subject without disturbing the subject's position while it is fixed to the bed 16, it is preferable to leave the animal's tail, legs, and eyes accessible while the animal is fixed to the bed 16. It is desirable to autoclave elements that have been in contact with animals, so those particular components are preferably resistant to high temperature steam cleaning and disinfection.

The beds are independently removable to facilitate access to subjects in multi-animal configurations. With rat and mouse subjects, heated tail holders are preferable because they help prevent tail veins from contracting in a cold environment and altering blood flow rates. Moreover, the beds 16 include heating mechanisms 33 for controlling the subject's temperature while attached to the bed 16. This can be built-in tubing for temperature control, such as embedded tubes in the base of the bed 16 that would allow for the circulation of heated water or air. In another embodiment the bed could include resistive coils and electrical connections. The temperature of the bed can be controlled by a thermostat that can turn on or off the heating of water, air, or resistive coils.

Absorbent materials can be included to handle excretion during imaging sessions; the bed design can accommodate disposable materials, or they can be integrated into the bed 16. The bed 16 can be designed with all or most of desired probes embedded into the bed 16. Alternately, the bed can be designed with all probes flexible enough to be placed wherever they are required by the operator. The integrated sensors 20 are useful for standardized imaging, specifically where throughput is an issue. External probes can be used, e.g., in complex research scenarios, where it is more desirable to execute a given scenario with maximum accuracy.

With reference again to FIG. 1, the system 10 also includes an animal positioner 34 capable of receiving and docking the capsule 14. The positioner 34 is used to position the animal capsule 14 optimally in an imaging region of the scanner 12 during an imaging session. The capsule 14 has an identifier to provide a unique holder identity to the system. The identity can be read when the capsule 14 is connected to the animal positioner 34, e.g. a bar code that moves past a reader during insertion. Fixed laser devices can also be used to aid in registration. A docking station 36 provides anesthesia and monitoring while the animal capsule 14 is attached awaiting a scan. As shown, the docking station may include storage space 38 for storage of additional beds 16 cylinders 18 or other devices when not in use. Although the animal preparation and imaging modules are contemplated and shown side by side, animal preparation and imaging may be located in separate rooms.

Figure 7:
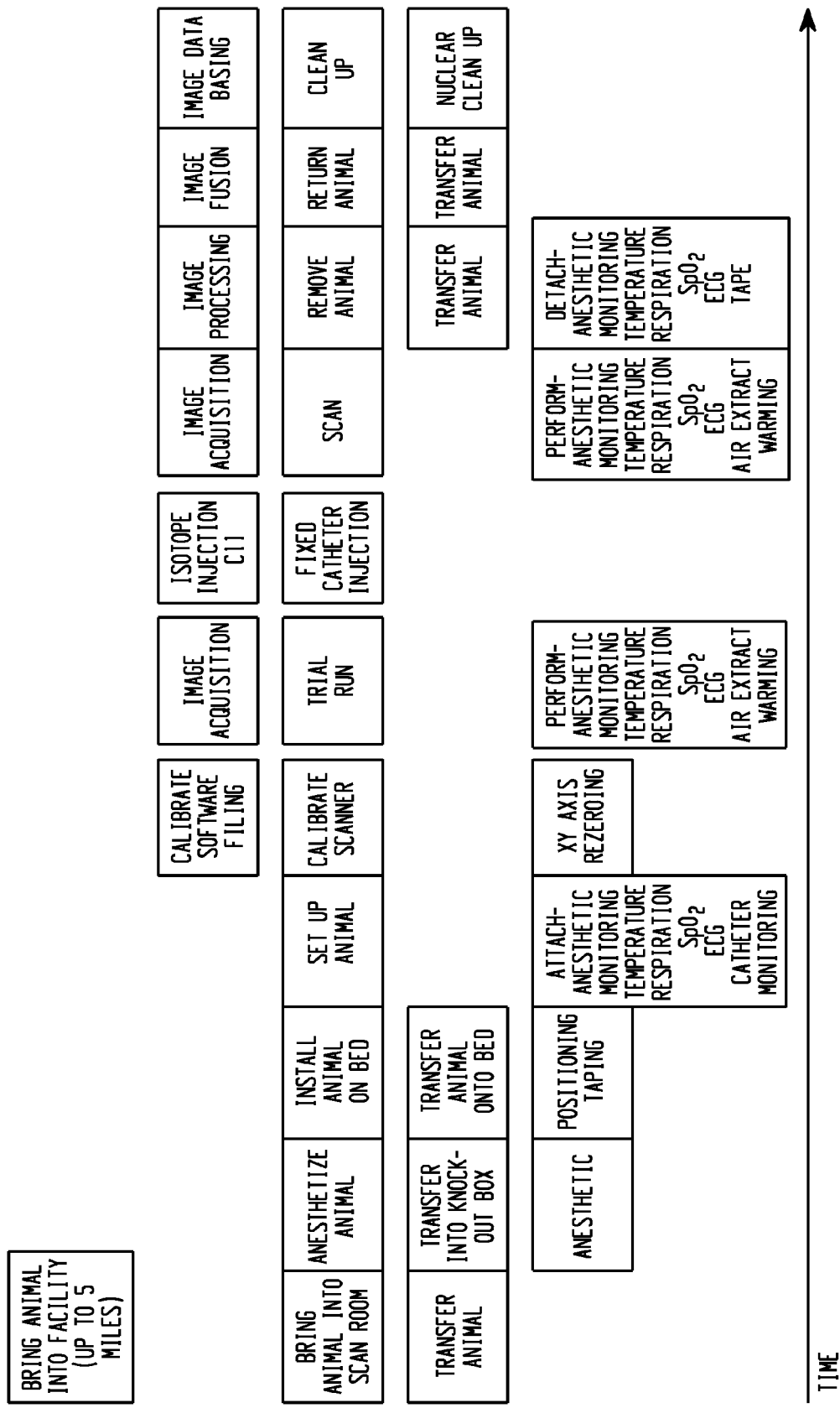
FIG. 7 illustrates an exemplary workflow timeline.

A side-by-side configuration of the modules 12, 12', 36 is preferred because it facilitates ease of workflow. The user does not have to be constantly walking back and forth across a room, or between rooms. An exemplary workflow is depicted in FIG. 7. In particular, it is a workflow for a PET imaging sequence. In such a workflow, there is potential for down time when the animal is actually being scanned. The radioisotope only decays so fast. In such a workflow, it becomes advantageous to prepare subsequent animals while one is being imaged, so that when the first scan is complete, a subsequent animal is ready to be imaged with no additional prep time. The workflow of FIG. 7, or one similar to it, happens for each animal, but the docking station 36 allows these workflows to substantially overlap, reducing overall work time, and increasing subject throughput.

In an illustrative example, say a typical animal scan takes ten minutes, which includes five minutes of prep time, and five minutes of scan time. To scan six animals would take an hour, if the workflow were repeated from start to finish for each animal. This includes time when the scanner is not scanning. The docking station 36 allows pre-preparation of the animals. While the first animal is being scanned, the second animal will be prepped and held at the docking station 36. Thus, the same task of scanning six animals is performed in only 35 minutes, with the only down time of the scanner being while the first animal is being prepped.

Figure 8:
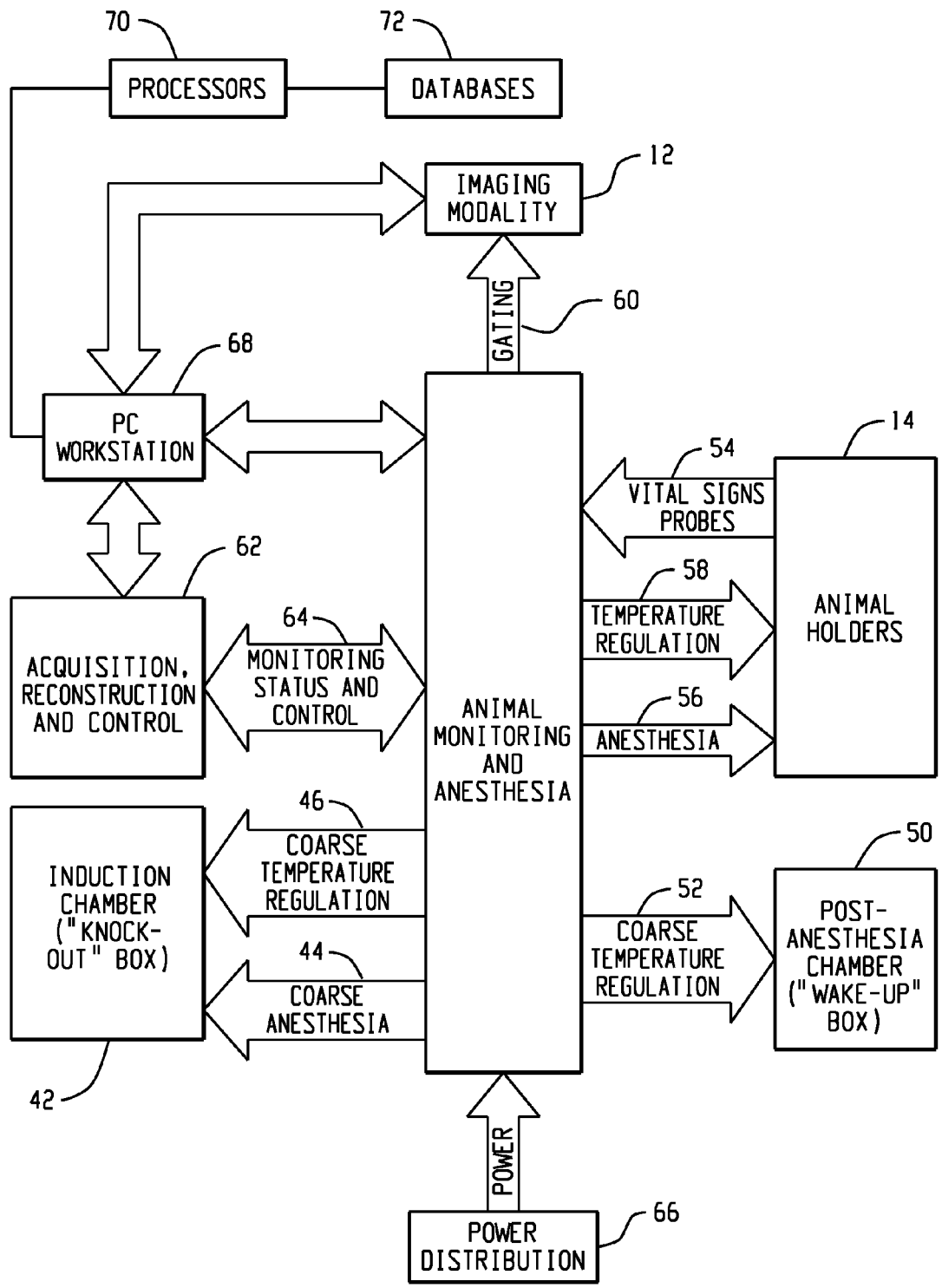
FIG. 8 illustrates relationships between the hardware aspects of the present application.

In the embodiment of FIG. 1, the system 10 includes three modules, namely first and second acquisition modules 12, 12' and the animal preparation module, that is, the docking station 36. Of course, fewer or greater numbers of modules are contemplated. Preferably, the docking station 36 adds several aspects of functionality. With reference to FIG. 8, an animal monitoring and anesthesia (AMA) system 40 is shown. An induction chamber 42 provides an area in which a conscious animal is placed so it can be anesthetized before it is mounted on the animal bed 16. Before an imaging session can begin, the animal is placed in the induction chamber 42 where it is given preliminary anesthesia before further preparations will take place. Anesthetic agent is provided via a coarse anesthesia interface 44. The subject's temperature is coarsely maintained with the use of heaters that rely on the environment or heater temperature. This control path is executed over a coarse temperature regulation interface 46.

A physical workspace 47 is provided at the docking station 36 to attach the subject to a bed 16 and install the required sensors 20, after the subject has been anesthetized in the induction chamber 40. Docking ports 48 for continuation of life support and anesthesia of the subject between studies are provided at the docking station 36 within close proximity to the positioner 34. Preferably, the number of docking ports 48 in the docking station matches the number of modalities available in the imaging facility (i.e. one docking slot per one available modality). Early preparation of a greater number of animals would not increase the imaging throughput, as imaging time is typically fixed, and is the factor that limits throughput. This way, the prepared animals spend no more time anesthetized than is necessary.

A post anesthesia chamber 50 or "wake up box" provides life support during wake-up of the subjects. Here, the subject's temperature is coarsely maintained via a coarse wakeup temperature regulator 52 in the same manner as it is done for subject in the induction chamber 42. The post anesthesia chamber 50 is preferably well ventilated to speed the subject's recovery from anesthesia.

The preferred method of docking the capsule 14 to the receiving system is through a positive locking mechanism that is engaged through axial force applied by means of an actuator placed in the positioner 34. Again, engagement of the actuator should not require disturbance of the animal. The docking interface 24 on each capsule 14 includes leads to engage the AMA system 40, including electrical and gas connections. The anesthesia connection includes an "auto shut-off on disconnection" function to prevent loss of anesthesia to the environment.

During a procedure the subject is located on the imaging bed 16 and attached to either the docking station 36 or the imaging modality 12. Its physiological parameters are monitored via a vital signs probes interface 54. Anesthesia is supplied and controlled via an anesthesia interface 56. This interface 56 can be a pneumatic interface that delivers anesthetic agent to the animal in the capsule 14 and extracts waste gases, but it can also include electrical (automatic) control of the agent concentration. Also the animal's core temperature is maintained with a temperature regulation interface 58 based on the current temperature measurement and desired target temperature value. The temperature regulation interface 58 preferably carries control signals that drive the heating elements working on per animal basis.

The AMA 40 also interfaces with one or more imaging modalities 12. In the preferred embodiment, the modality's operation does not depend on the AMA 40. For certain studies, however, physiological gating information is required in order to correctly build an image. A gating signal can be passed over a gating interface 60 that is the same for all imaging modalities. The gating interface 60 is preferably a TTL (0-12V) interface that accepts an active state as a gate event for image reconstruction.

An acquisition, reconstruction and control subsystem 62 also interfaces with the AMA 40. The subsystem 62 has at least two functions related to the AMA 40. These functions include presentation and storage of acquired vital signs data, control of monitoring and anesthesia functions, image reconstruction, correlation of vital signs data with image data, and the like. These commands and data are sent over a monitoring status and control interface 64. The interface 64 can handle all monitoring data, status and control commands. It is to be understood that acquisition, reconstruction, and control are logical components that are physically distributed over different parts of the system 10. A power distribution unit 66 distributes electric power to all subsystems.

The system also includes a computer workstation 68. The workstation 68 includes a computer that controls main system functions and provides an interface for a user to work with the image and vital signs data. The workstation 68 includes acquisition control to allow starting, pausing, resuming and stopping an image acquisition and showing status and progress info on the acquisition. The workstation 68 also interfaces with the AMA 40 in order to display vital signs for multiple animals scanned across several modalities and stages of animal preparation on the workstation. Additionally, acquisition control and a reconstruction user interface reside on the workstation 68. Multimodality function is included on the workstation 68 such as PET-CT non-rigid registration. In such a situation, interfacing with a CT Acquisition control can to be done via the workstation 68. It is preferable that the workstation 68 provides a migration path for all applications of the system 10 to use a common platform for infrastructure services and operation. Naturally, the workstation 68 can be upgraded as new preparation techniques, scanning techniques, software, hardware, and the like become available. Alternatively, the AMA 40 is capable of running without an associated workstation 68; however, functionality and accessibility to the AMA 40 would be more limited.

Figure 9:
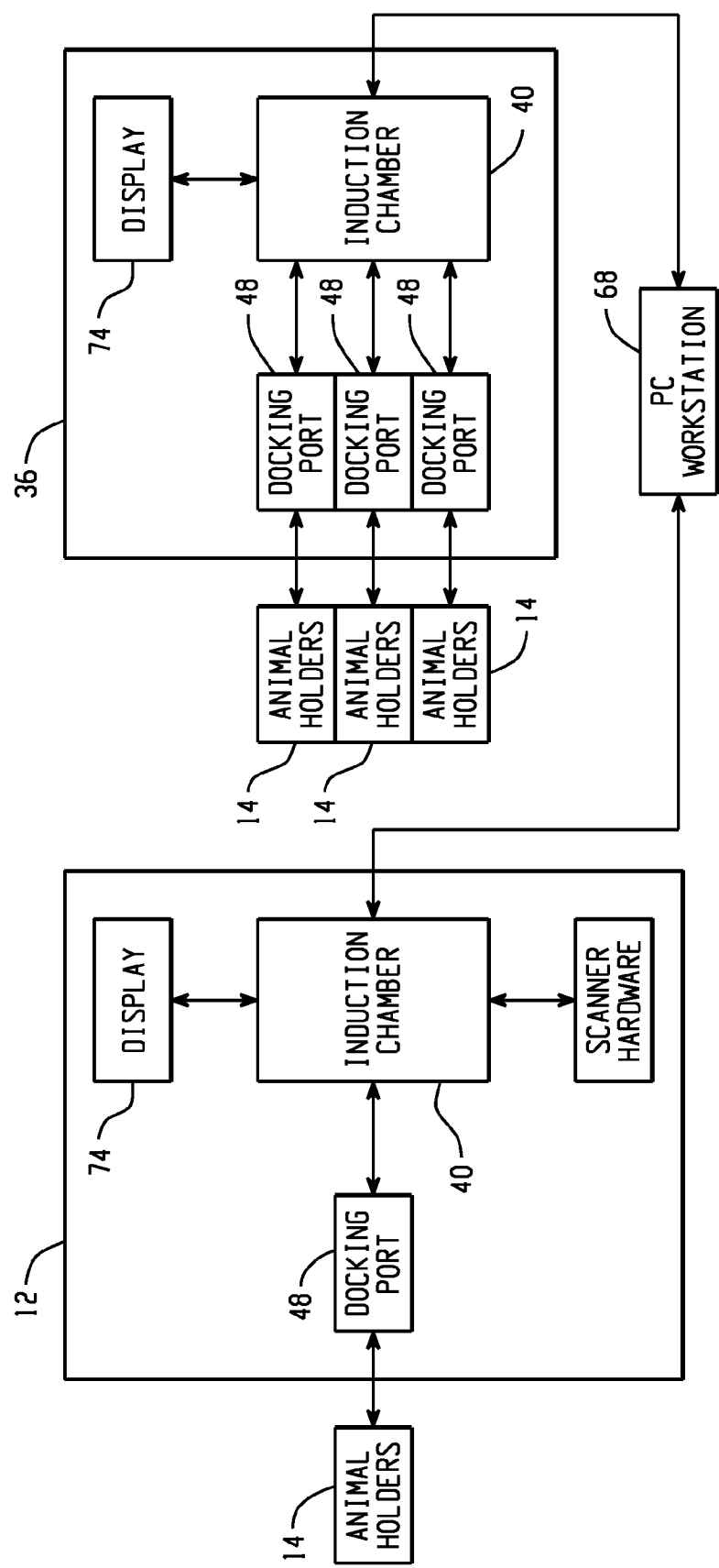
FIG. 9 is a schematic diagram of one possible implementation of the system of FIG. 1.

The workstation 68 presents information to the user and allows the user to enter data into the system. Optionally, the workstation 68 itself does not process information, it merely passes and receives it to/from behind-the-scenes processing 70, storing and retrieving data from databases 72, and the like. The workstation's 68 tasks include presenting results of monitoring and anesthesia, entering animal identification and tracer injection times, configuring gating signal, and the like. For entering experiment information and configuration settings an input device, such as a keyboard or mouse, is used. The workstation need not be a PC; it could be, for example, a display 74 on the modality 12 such as a touch screen. FIG. 9 shows, in schematic form, one possible implementation of the system 10.

In another embodiment, a portable AMA can be provided. To increase docking station's usage flexibility it is preferable that function in this embodiment is limited to docking capabilities. Preparation stations may vary significantly by size and complexity between different imaging facilities, therefore, it is preferred that the facility organizes the station wherever it suits them and their own needs. Then, the docking station can be placed either aside the preparation station providing storage for prepared animals, or it can be placed aside modalities, which often can be in different rooms, offering temporary storage for longer studies or when animal is exchanged between different modalities. Portability of such a unit would allow it to be placed wherever it is convenient. Also, its functional similarity to the normal AMA unit would allow technicians for early detection of wrong animal setup or monitoring and anesthesia defects.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. An imaging system comprising:
    a plurality of imagers, and each imager is configured to acquire diagnostic imaging data of subjects in one of a plurality of animal capsules located in an imaging region of one of the imagers, and each imager having at least a first docking interface which connects to a uniform capsule interface of the one of the plurality of animal capsules during imaging;
    a docking station adapted to prepare subjects for imaging in at least one of the plurality of imagers, the docking station including:
        at least a second docking interface which is adapted to connect to the uniform capsule interface of the at least one of the plurality of animal capsules and hold the at least one of the plurality of animal capsules while each subject is secured in the at least one of the plurality of animal capsules,
        an induction chamber adapted to hold and anesthetize the subjects before each subject is secured in the at least one of the plurality of animal capsules; and
    wherein, each animal capsule of the plurality of animal capsules is adapted to enclose a plurality of subjects for simultaneous imaging in each of the plurality of imagers and includes:
        at least two subject supports, each support adapted to support a sedated subject during preparation and imaging;
        a removable cover adapted to encapsulate the at least two subject beds; and the uniform capsule interface adapted to connect with the at least first docking interface of each imager and the at least second docking interface of the docking station.

2. The imaging system as set forth in claim 1, wherein the plurality of imaging scanners include at least one of a small animal PET scanner, CT scanner, SPECT scanner, or a MRI scanner, or a hybrid scanner containing at least two imaging modalities.

3. The imaging system as set forth in claim 1, wherein the docking station includes a post-anesthesia chamber adapted to hold an anesthetized animal after an imaging session to allow the animal to recover from anesthesia.

4. The imaging system as set forth co in claim 1, wherein the docking station includes a workspace configured to allow a user to prepare an anesthetized animal for imaging.

5. The imaging system as set forth in claim 1, wherein each subject support is a contoured support adapted to assist in positioning and image registration of an animal.

6. The imaging system as set forth in claim 1, wherein the animal capsule includes at least three subject supports and the at least three subject supports are enclosed by the removable cover.

7. The imaging system as set forth in claim 1, wherein each animal capsule includes:
at least one sensor integrated into the subject support for monitoring at least one biological function of the subject located on the subject support; and
wherein the uniform capsule interface includes electrical connections for facilitating communication of the at least one sensor with a monitoring device.

8. The imaging system as set forth in claim 1, wherein the uniform capsule interface of each animal capsule includes electrical connections and fluid connections.

9. The imaging system as set forth in claim 8, wherein each animal capsule includes a nosecone for each subject that is supplied by the fluid connections and adapted to keep an animal in an anesthetized state during imaging in the imagers, and adapted to hold in anticipation of imaging and connected to the docking station.

10. The imaging system as set forth in claim 1, wherein the subject support includes at least one sensor device adapted to measure at least one biological process of the animal during imaging while the at least one animal capsule is connected to one of the scanners, and during holding or preparation while the at least one animal capsule is connected to the docking station.

11. The imaging system as set forth in claim 10, further including:
an alarm system for alerting a user when at least one abnormal biological process of at least one subject in the at least one animal capsule is detected during imaging in the at least one imager, or holding while connected to the docking station.

12. The imaging system as set forth in claim 1, wherein the at least two subject supports include a heating element for controlling the environment within the capsule.

13. The imaging system as set forth in claim 12, wherein the heating element includes a tail warming portion adapted to warm the tail of the animal mounted to the support.

14. The imaging system as set forth in claim 1, wherein each subject support includes fiducials adapted to be imaged by at least one of the imaging scanners to aid in registration of images.

15. The imaging system as set forth in claim 14, wherein the fiducials are adapted to be imaged by the imaging scanners.

16. The imaging system as set forth in claim 1, wherein each of the imaging modalities further includes:
a positioner connected to the first docking interface for positioning the capsule in the imaging modality.

17. The imaging system as set forth in claim 16, wherein the positioner is adapted to position the capsule from behind the modality, relative to where a user attaches the capsule to the docking interface.

18. The imaging system as set forth in claim 1, wherein the subject support includes a registration system configured to aid in image registrations.

19. The imaging system as set forth in claim 18, wherein the registration system includes at least one of the subject supports contoured to conform to a natural disposition of the subject, to reproduce subject position across imaging scans.

20. The imaging system as set forth in claim 18, wherein the registration system includes a plurality of fiducials associated with each subject support arranged in a non-linear fashion adapted to be viewed by each of the imagers.

21. An imaging system comprising:
at least one animal capsule which includes:
a plurality of subject supports, each configured to support an anesthetized animal during imaging and preparation, each subject support including:
at least one sensor device that is configured to measure at least one biological process of the animal while it is mounted to the support;
electrical leads connected to the sensors and configured to supply the sensors with power and carry communication signals indicative of at least one biological process of each mounted animal;
a removable cover configured to enclose the plurality of subjects and the subject supports;
a uniform capsule interface configured to connect to the electrical leads and receive the communication signals indicative of the at least one biological process of each mounted animal;
at least one imaging module which includes a small animal scanner configured to acquire diagnostic imaging data of the subjects in an imaging region of the scanner and in the at least one animal capsule, the scanner having at least a first docking interface configured to connect to the uniform docking interface during imaging and receive the electrical signals indicative of the at least one biological process of each mounted animal to a monitoring device; and
a docking station configured to prepare the subjects for imaging in the imaging scanner, the docking station having at least a second docking interface configured to connect to the uniform docking interface during preparation and holding, and provide the communication signals indicative of the at least one biological process of each mounted animal to the monitoring device.

22. An imaging system comprising:
at least one imager configured to acquire diagnostic imaging data and generate diagnostic images of subjects simultaneously in an imaging region of the imager, the imager having at least a first docking interface;
a docking station configured to prepare subjects for imaging in the imager, the docking station including at least a second docking interface and an induction chamber configured for anesthetizing the subject before securing the subject in an at least one animal capsule; and
the at least one animal capsule being configured to enclose a plurality of subjects and interface with the first and second docking interfaces, and includes:

a plurality of subject supports, each subject support configured to support an anesthetized animal during imaging and preparation, and each subject support being contoured to the size and shape of the type of subject for securing subjects in reproducible subject positions to aid in inter-subject and intra-subject registrations; and a removable cover configured to enclose the plurality of subject supports.

23. A method of imaging comprising:

anesthetizing a plurality of animal subjects;

affixing each of the animal subjects to an imaging subject support;

encapsulating the animal subjects and the bed with a cover forming an animal capsule with a uniform capsule interface;

connecting the uniform capsule interface of the animal capsule to a docking interface of a docking station;

providing vital signs monitoring of the animal subjects, anesthesia delivery, and waste gas removal while the animal capsule is docked to the docking station;

disconnecting the uniform capsule interface of the animal capsule from the docking interface of the docking station and connecting the uniform capsule interface of the capsule to a docking interface of an imaging scanner;

positioning the animal capsule within an imaging region of the scanner;

performing an imaging scan of the animal subjects within the animal capsule;

providing vital signs monitoring of the animal subjects, continued anesthesia delivery, and waste gas removal while the animal capsule is docked to the imaging scanner.

24. The method as set forth in claim 23, wherein continued anesthesia delivery and waste gas removal are provided through pneumatic connections located in the uniform capsule interface of the animal capsule, and vital signs monitoring is provided via electrical connections in the uniform capsule interface of the animal capsule.

* * * * *